United States Patent [19]

Carson

[11] 4,119,639
[45] Oct. 10, 1978

[54] PREPARATION OF 5-AROYLPYRROLE-2-ACETIC ACID DERIVATIVES

[75] Inventor: John Robert Carson, Norristown, Pa.

[73] Assignee: McNeil Laboratories, Incorporated, Ft. Washington, Pa.

[21] Appl. No.: 809,956

[22] Filed: Jun. 27, 1977

[51] Int. Cl.$^2$ .................. C07D 207/32; C07D 207/34
[52] U.S. Cl. ........................... 260/326.35; 260/326.47; 260/326.5 SM; 260/326.5 J; 260/327 M
[58] Field of Search ................ 260/326.47, 326.55 M, 260/326.35, 326.5 J, 327 M

[56] References Cited

U.S. PATENT DOCUMENTS

| | | | |
|---|---|---|---|
| 2,690,988 | 10/1954 | Jones et al. | 260/327 M |
| 3,803,171 | 4/1974 | Carson | 260/326.47 |
| 3,846,447 | 11/1974 | Carson | 260/326.47 |
| 3,947,469 | 3/1976 | Ghosey et al. | 260/327 M |
| 3,998,844 | 12/1976 | Carson | 260/326.47 |
| 4,048,191 | 9/1977 | Carson | 260/326.47 |

OTHER PUBLICATIONS

Corey et al.; J. Org. Chem., vol. 36, pp. 3553–3560, (1971).

Primary Examiner—Donald G. Daus
Assistant Examiner—Mary C. Vaughn
Attorney, Agent, or Firm—Salvatore R. Conte

[57] ABSTRACT

The interaction of a 2-aryldithiolanium cation with an appropriate pyrrole-2-acetic acid derivative to give a 5-[2-aryl-2-(1,3-dithiolanyl)]pyrrole-2-acetic acid derivative which is then converted to the corresponding 5-aroylpyrrole-2-acetic acid derivative.

5 Claims, No Drawings

PREPARATION OF 5-AROYLPYRROLE-2-ACETIC ACID DERIVATIVES

BACKGROUND OF THE INVENTION

The end products of the process of this invention belong to the class of 5-aroylpyrrole-2-acetic acid derivatives having anti-inflammatory activity (e.g., see U.S. Pat. Nos. 3,752,826; 3,803,169; 3,846,447 and 3,957,818). The subject invention offers an alternate improved process for making such derivatives. Among these derivatives is the important commercially available anti-inflammatory agent generically known as "tolmetin".

DESCRIPTION OF PREFERRED EMBODIMENTS

This invention relates to a method of preparing 5-aroylpyrrole-2-acetic acid derivatives of the formula:

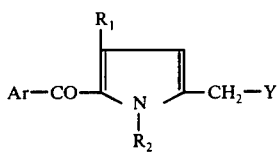

wherein:
$R_1$ is a member selected from the group consisting of hydrogen and halo, preferably chloro and bromo;
$R_2$ is a member selected from the group consisting of hydrogen and loweralkyl, preferably methyl;
Y is a member selected from the group consisting of CN, COOH and COO-loweralkyl; and
Ar is a member selected from the group consisting of phenyl, thienyl, trifluoromethylphenyl, methylthiophenyl and phenyl substituted with from one to three members each selected from the group consisting of halo, loweralkyl (preferably methyl) and loweralkoxy (preferably methoxy).

As used herein, "loweralkyl" refers to straight or branch chained alkyls having from 1 to 6 carbons, for example, methyl, ethyl, propyl, isopropyl, butyl, tert-butyl, pentyl, hexyl and the like; "loweralkoxy" refers to the corresponding alkoxys, for example, methoxy, ethoxy, propoxy, isopropoxy, etc.; and "halo" refers to chloro, bromo, fluoro, and iodo.

According to the instant process, an appropriate 2-aryldithiolanium cation (II), wherein Ar is as previously described and $R_3$ is a member selected from the group consisting of hydrogen and loweralkyl, is reacted with an appropriate pyrrole-2-acetic acid derivative (III), wherein $R_1$ and $R_2$ are as previously defined and $Y_1$ is CN or COO-loweralkyl, to yield the corresponding 5-[2-aryl-2-(1,3-dithiolanyl)]pyrrole-2-acetic acid derivatives (IV). The reaction is preferably conducted in an inert organic solvent such as, for example, an aromatic hydrocarbon, e.g., benzene, toluene, xylene and the like; a halocarbon, e.g., methylene chloride, chloroform, dichloroethane and the like; and ether, e.g., diethyl ether, tetrahydrofuran (THF), dioxane and the like; a nitrile, e.g., acetonitrile; an ester, e.g., ethyl acetate; and the like. The temperature of the reaction may range from about −70° C. to about 25° C. and, preferably, about 0°–10° C.

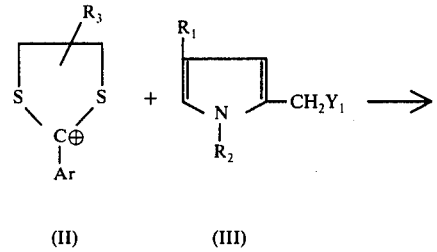

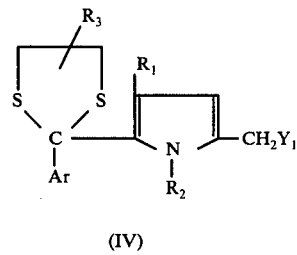

The thus-obtained 5-[2-aryl-2-(1,3-dithiolanyl)]pyrrole-2-acetic acid derivative (IV) may then be converted to the desired end products of formula (I) by treatment with an appropriate alkylating agent, such as, for example, dimethyl sulfate and, preferably, methyl iodide, in a lower alkanolic solvent with 1–10% water, thereby causing hydrolysis to the corresponding 5-aroyl compounds of (I). Elevated temperatures and, preferably, the reflux temperature of the solvent, may be advantageously employed to enhance the rate of reaction.

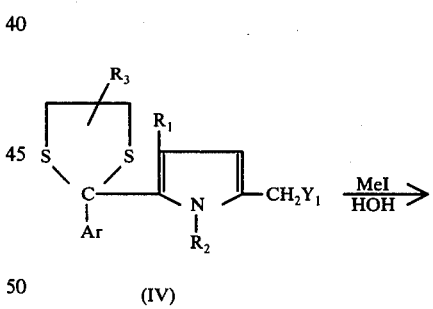

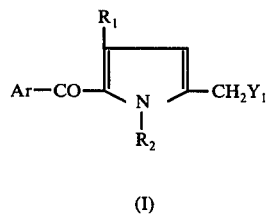

Alternatively, alkaline hydrolysis of (IV), e.g., with alkali, such as, for example, sodium or potassium hydroxide in aqueous or aqueous alkanolic solution (e.g., EtOH, ethylene glycol and the like), at elevated temperatures of about 70°–180° C. and, preferably, about 150° C., affords the 5-aroyl acids of formula (I-a).

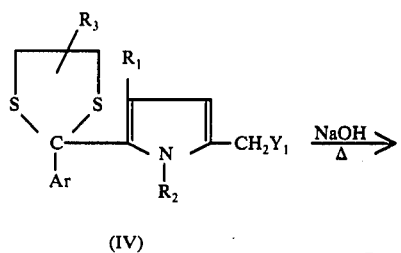

(IV)

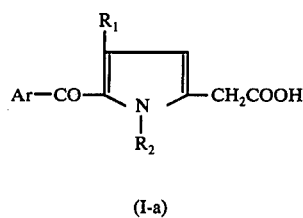

(I-a)

The 2-aryldithiolanium cations of formula (II), in the form of their corresponding 2-aryl-1,3-dithiolanium salts of the formula:

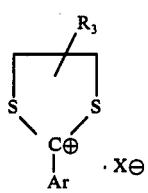

(II-a)

wherein Ar and $R_3$ are as previously defined and X is a non-nucleophilic anion such as, for example, fluoborate ($BF_4^-$), perchlorate ($ClO_4^-$), hexafluorophosphate ($PF_6^-$), hexafluoroantimonate ($SbF_6^-$) and the like, can be prepared by treating (hydride abstraction) the corresponding 2-aryl-1,3-dithiolane (V) with an appropriate trityl salt of formula (VI) in an inert polar solvent such as, for example, acetonitrile, $SO_2$ (liquid) and the like at temperatures from about $-50°$ C. to about $25°$ C.

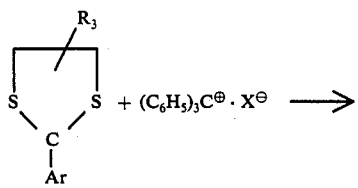

(V)   (VI)

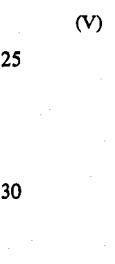

(II-a)

The 2-aryl-1,3-dithiolanium salts with non-nucleophilic cations (II-a) can be isolated as substantially pure substances and characterized by standard techniques. They exhibit strong characteristic ultra violet (U.V.) absorption in the range 360–390 nm.

The process of this invention may also be carried out by reacting a solution of reagents which liberate the aforementioned 2-aryl-1,3-dithiolanium cation (II) in situ (detectable by U.V. absorption at 360–390 nm) with an appropriate pyrrole-2-acetic acid derivative (III). Such preferred solutions are those obtained by the halogenation (chlorination or bromination) of 2-aryl-1,3-dithiolanes of formula (V) with an appropriate halogenating agent such as, for example, chlorine, bromine, N-chlorosuccinimide, N-bromosuccinimide, sulfuryl chloride and the like in an appropriate reaction-inert organic solvent to yield the dithiolanium halide salt of formula (II-b). The preferred chlorinating agent is sulfuryl chloride.

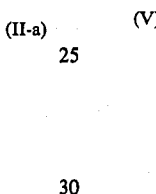 + halogenating agent ⟶

(V)

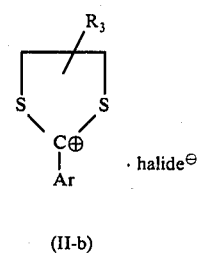

(II-b)

An alternative method of providing the 2-aryl-1,3-dithiolanium cations of formula (II) in solution is by the reaction of an appropriate N,N-di-(loweralkyl)-arylcarboxamide (VII) with a chlorinating agent selected from the group consisting of phosphoryl chloride, thionyl chloride, phosgene, oxalyl chloride and the like to yield the corresponding Vilsmeier reagent of formula (VIII), wherein Z is a member selected from the group consisting of $Cl^\ominus$ and $PO_2Cl_2^\ominus$, which is then reacted with ethanedithiol (IX) to yield the 2-aryl-1,3-dithiolanium cation of formula (II-c) in situ.

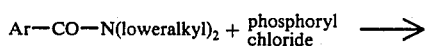

(VII)

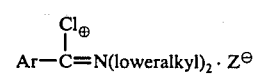

(VIII)

(VIII) + HS—$CH_2CH_2$—SH ⟶ 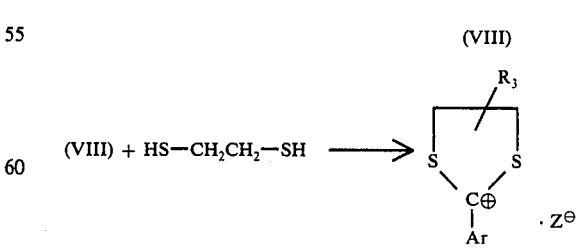

(II-c)

Another method of preparing the 2-aryl-1,3-dithiolanium cations of formula (II) is by treating an appropriate arylthiolane derivative of formula (X) with a strong acid, e.g., HCl, H₂SO₄, H₃PO₄, methanesulfonic acid, toluene sulfuric acid and the like in an appropriate reaction-inert organic solvent.

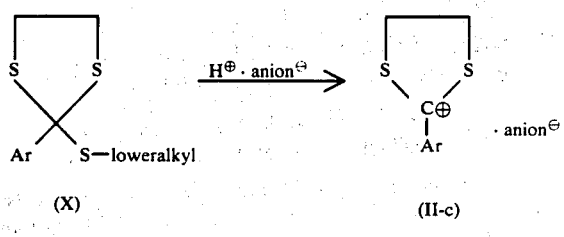

An example of an easily accessible arylthiolane of formula (X) is the bis-compound of formula (XI) obtained by treatment of 2 equivalents of the aforementioned Vilsmeier reagent (VIII) with 3 equivalents of ethanedithiol.

2 (VIII) + 3 HS—CH₂CH₂—SH ⟶

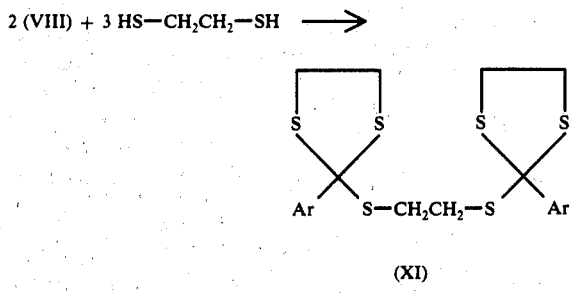

EXAMPLE I

A. 5-[2-(4-Methylphenyl)-2-(1,3-dithiolanyl)]-1-methylpyrrole-2-acetonitrile

A mixture of 17.9 g (0.11 mole) of N,N-dimethyl-4-methylbenzamide and 10.05 ml (0.11 mole) of phosphous oxychloride is heated at 60° for 2 hr under nitrogen. A 30 ml portion of 1,2-dichloroethane is added. A solution of 9.3 ml (0.11 mole) of 1,2-ethanedithiol in 30 ml of 1,2-dichloroethane is added dropwise at a rate such that the temperature remained at 40°-50° C. The mixture is stirred for 30 min. The resulting solution is added dropwise to 12.0 g (0.10 mole) of 1-methylpyrrole-2-acetonitrile in 200 ml of 1,2-dichloroethane at 10° over 90 min. The mixture is stirred 60 min at 10°. The solution is poured into 10% sodium hydroxide solution at 5°. The organic layer is separated, washed with brine, and dried. The solvent is evaporated in vacuo. The residue is crystallized from ethylacetate-methyl cyclohexane to give 19.6 g of white crystalline 5-[2-(4-methylphenyl)-2-(1,3-dithiolanyl)]-1-methylpyrrole-2-acetonitrile, m.p. 124°-126° C., yield 61%. Further recrystallization from ethyl acetate gives solid, m.p. 129°-131° C.

B. 5-[2-(4-Methylphenyl)-2-(1,3-dithiolanyl)]-1-methylpyrrole-2-acetonitrile

A mixture of 180 g (1.1 mole) of N,N-dimethyl-4-methylbenzamide and 168 g (1.1 mole) of phosphous oxychloride is heated til an exothermic reaction occurs. The temperature is maintained below 70° with cooling. It is heated at 60° for 2.5 hr. A 300 ml portion of 1,2 dichloroethane is added. A solution of 106 g (1.1 mole) of ethanedithiol in 300 ml of 1,2-dichloroethane is added so the temperature stays between 45° and 55° C. After stirring for 30 min, the solution is cooled to 10° C. A solution of 120 g (1.0 mole) of 1-methylpyrrole-2-acetonitrile in 900 ml of 1,2-dichloroethane is added. The mixture is stirred 45 min at 5°-10° C. It is poured into 4 l of 5% sodium hydroxide solution. The organic layer is separated, washed with brine, and dried over MgSO₄. The solvent is evaporated in vacuo. The residue is recrystallized from ethyl acetate to give 218 g (69% yield) of 5-[2-(4-methylphenyl)-2-(1,3-dithiolanyl)] 1-methylpyrrole-2-acetonitrile.

C. 5-[2-Aryl-2-(1,3 dithiolanyl)]-1-methylpyrrole-2-acetonitriles

The procedure of Example IA is followed substituting the following N,N-dimethyl aryl carboxamides for 4-methyl-N,N-dimethylbenzamide:
4-chloro-N,N-dimethylbenzamide;
N,N-dimethyl-4-fluorobenzamide;
N,N-dimethyl-4-methoxybenzamide;
N,N-dimethyl-4-trifluoromethyl benzamide;
N,N-dimethyl-2-thienylcarboxamide.

The products obtained respectively were as follows:
5-[2-(4-Chlorophenyl)-2-(1,3-dithiolanyl)]-1-methylpyrrole-2-acetonitrile, m.p. 168°-170° C.;
5-[2-(4-Fluorophenyl)-2-(1,3-dithiolanyl)]-1-methylpyrrole-2-acetonitrile, m.p. 81°-82° C.;
5-[2-(4-Methoxyphenyl)-2-(1,3-dithiolanyl)]-1-methylpyrrole-2-acetonitrile, m.p. 86°-87° C.;
1-Methyl-5-[2-(4-trifluoromethylphenyl)-2-(1,3-dithiolanyl)]-pyrrole-2-acetonitrile, m.p. 141°-142° C.;
1-Methyl-5-[2-(2-thienyl)-2-(1,3-dithiolanyl)]-pyrrole-2-acetonitrile, m.p. 108°-109° C.

EXAMPLE II

A. Sodium 5(-4-Methylbenzoyl)-1-methylpyrrole-2-acetate

A solution of 1.6 g (0.005 mole) of 5-[2-(4-methylphenyl)-2-(1,3-dithiolanyl)]-1-methylpyrrole-2-acetonitrile in 25 ml of ethanol plus 1.6 g of 50% sodium hydroxide solution is heated under reflux for 4 days. The solvent is evaporated and the residue recrystallized twice from ethanol to give 0.47 g of yellow solid sodium 5-(4-methylbenzoyl)-1-methylpyrrole-2-acetate, found identical by thin layer chromatography (TLC) to authentic tolmetin.

B. Sodium 5-(4-Methylbenzoyl)-1-methylpyrrole-2-acetate

A 9.63 g (0.03 mole) sample of 5-[2-(4-methylphenyl)-2-(1,3-dithiolanyl)]-1-methylpyrrole-2-acetonitrile in 50 ml of ethanol is heated under reflux and a solution of 4.8 g (0.12 mole) of sodium hydroxide in 20 ml of water is added dropwise over 30 min. It is heated under reflux for 2 hr. It is transferred to an autoclave and 100 ml of 50% aqueous ethanol is added. It is heated with stirring at 145° C. for 18 hr. The bomb is cooled and the contents triturated with warm 50% aqueous ethanol. This mixture is filtered while hot. The filtrate is concentrated to about 20 ml and 50% aqueous sodium hydroxide solution is added and the precipitated solid is collected. The solid is boiled with 80% ethanol. The solution is decanted from solid. The solid sodium 5-(4-methylbenzoyl)-1-methylpyrrole-2-acetate which separated from the solution on cooling weighed 4.55 g (48% yield).

C. Sodium 5-(4-methylbenzoyl)-1-methylpyrrole-2-acetate

A mixture of 10 g of 5-[2-(4-methylphenyl)-2-(1,3-dithiolanyl)]-1-methylpyrrole-2-acetonitrile. 10 g of 50% sodium hydroxide solution and 50 ml of ethylene glycol is heated at 135° C. After 4 hr, the mixture is cooled and acidified with hydrochloric acid. The solid is collected. It is dissolved in tetrahydrofuran. Upon addition of 25% sodium hydroxide solution a precipitate of sodium 5-(4-methylbenzoyl)-1-methylpyrrole-2-acetate forms. It is collected by filtration and dried to give 5.7 g (56% yield) of sodium 5-(4-methylbenzoyl)-1-methylpyrrole-2-acetate.

EXAMPLE III

A. 4-Methylbenzoyl-1-methylpyrrole-2-acetonitrile

A solution of 618 mg (1.96 mmoles) of 5-[2-(4-methylphenyl)-2-(1,3-dithiolanyl)]-1-methylpyrrole-2-acetonitrile and 1.49 ml (16.0 mmoles) of methyl iodide in 25 ml of 96% methanol, 4% water is heated under reflux for 18 hr. It is poured into sodium bicarbonate solution and extracted with methylchloroform. The organic solution is separated, dried (MgSO₄), and concentrated in vacuo. The residue is crystallized from methylcyclohexane to give 180 mg of white solid, m.p. 99°–101° C., identical to authentic 4-methylbenzoyl-1-methylpyrrole-2-acetonitrile by TLC and mixed m.p.

B. 5-Aroyl-1-methylpyrrole-2-acetonitriles

The procedure of Example IA is followed substituting the following 5-[2-aryl-2(1,3-dithiolanyl)]-1-methylpyrrole-2-acetonitriles for 5-[2-(4-methylphenyl)-2-(1,3-dithiolanyl)]pyrrole-2-acetonitrile:

5-[2-(p-Fluorophenyl)-2-(1,3-dithiolanyl)]-1-methylpyrrole-2-acetonitrile; and
1-Methyl-5-[2-(4-methoxyphenyl)-2-(1,3-dithiolanyl)]pyrrole-2-acetonitrile;
1-Methyl-5-[2-(4-trifluoromethylphenyl)-2-(1,3-dithiolanyl)]pyrrole-2-acetonitrile;

The products obtained respectively are:
5-(4-fluorobenzoyl)-1-methylpyrrole-2-acetonitrile, m.p. 135°–136° C.;
5-(4-methoxybenzoyl)-1-methylpyrrole-2-acetonitrile, m.p. 145°–146° C.; and
1-Methyl-5-(4-trifluoromethylbenzoyl)pyrrole 2-acetonitrile, m.p. 94°–95° C.

All were identical by mixed melting point with authentic samples.

EXAMPLE IV

A. 2,2'-[1,2-Ethanediylbis (thio)]-2,2'-di(4-methylphenyl)bis(1,3-dithiolane)

A 16.3 g (0.1 mole) sample of N, N-dimethyl-4-methylbenzamide is heated to 60° under nitrogen and 9.15 ml (0.01 mole) of phosphorus oxychloride is added dropwise so that the temperature stays below 60°. It is heated for 2 hr at 60°. A 30 ml portion of 1,2-dichloroethane is added. A solution of 12.6 ml (0.015 mole) of ethanedithiol is added dropwise so the temperature stays between 30° and 40° C. The mixture is stirred 2 hr at 25°. It is poured into a mixture of ice and dilute sodium hydroxide solution. The mixture is extracted with 1,2-dichloroethane. The organic layer is washed with sodium hydroxide solution. The solvent is evaporated in vacuo. The residue is recrystallized from ethyl acetate to give a 12.0 g of a white solid. Further recrystallization from methanol gives 11.0 g of white solid 2,2'-[1,2-ethanediylbis (thio)]-2,2'-di(4-methylphenyl)bis(1,3-dithiolane), m.p. 118°–120° C. (39% yield).

B. 2,2'-[1,2-Ethanediylbis(thio)]-2,2' di(4-chlorophenyl)bis (1,3-dithiolane)

The procedure of Example IV is followed substituting 4-chloro-N,N-dimethyl benzamide for N,N-dimethyl-4-methyl benzamide. The product is 2,2'-[1,2-ethanediylbis(thio)] 2,2'-di (4-chlorophenyl)bis (1,3-dithiolane), m.p. 107°–109° C.

EXAMPLE V

5-[2-(4-Methylphenyl)-2-(1,3-dithiolanyl)]-1-methylpyrrole-2-acetonitrile

A solution of 4.82 g (0.01 mole) of 2,2'-[1,2-ethanediylbis (thio)]-2,2'-di(4-methylphenyl)bis (1,3-dithiolane) and 2.40 g (0.02 mole) of N-methylpyrrole-2-acetonitrile in 40 ml of 1,2-dichloroethane is stirred at 25° C. and a solution of 20 ml of 1% hydrochloride in 1,2-dichloroethane is added. The mixture is stirred 1¾ hr. It is poured into dilute sodium hydroxide. Chloroform is added. The organic layer is separated and dried (MgSO₄). The solvent is evaporated in vacuo. The residue is crystallized from methanol to give 5.9 g of a solid, m.p. 117°–123° C. Recrystallization from methylcyclohexane gives 3.2 g (50% yield) of 5-[2-(4-methylphenyl)-2-(1,3-dithiolanyl)]-1-methylpyrrole-2-acetonitrile.

EXAMPLE VI

5-[2-(4-Chlorophenyl)-2-(1,3-dithiolanyl)]-1-methylpyrrole-2-acetonitrile

The procedure of Example V is repeated except that an equivalent amount of the product of Example IV-B is utilized as the reactant with N-methylpyrrole-2-acetonitrile to yield 5-[2-(4-chlorophenyl)-2-(1,3-dithiolanyl)]-1-methylpyrrole-2-acetonitrile as the product.

EXAMPLE VII

2-(4-Methylphenyl)-1,3-dithiolanium fluoroborate

A 3.30 g (0.01 mole) sample of triphenylcarbenium tetrafluoroborate is added to a solution 3.92 g of 2-(4-methylphenyl)-1,3-dithiolane in 35 ml of acetonitrile under nitrogen at 5° C. Methylene chloride is added then ether. The yellow solid is collected and washed with ether. There is obtained 0.7 g (14% yield) of 2-(4-methylphenyl)-1,3-dithiolanium fluoroborate, m.p. 119°–120° C.

Anal calcd for $C_{10}H_{11}S_2.BF_4$: C, 42.57; H, 3.92. Found: C, 42.53; H, 3.99.

U.V.λmax (CH₂Cl₂), 243nm(ε=5,882), 272nm(ε=4,950), 374nm(ε=18,286).

EXAMPLE VIII

5-[2-(4-Methylphenyl)-2-(1,3-dithiolanyl)]-1-methylpyrrole-2-acetonitrile

A solution of 1.41 g (0.005 mole) of 2(4-methylphenyl)-1,3-dithiolanium fluoroborate in 7 ml of methylene chloride is added dropwise to a solution of 6.0 g (0.05 mole) of N-methylpyrrole-2-acetonitrile in 18 ml of methylene chloride at 5° C. under nitrogen over a period of 20 min. The solution is stirred for 5 min. It is shaken with iced dilute sodium hydroxide. The organic layer is dried (MgSO₄) and the solvent is evaporated in vacuo. The excess N-methylpyrrole-2-acetonitrile is flash evaporated at 100° C., 0.1 mm/Hg to give 1.0 g of a yellow oil. The oil is chromatographed on 60 g of silica gel. The column is eluted with mixtures of hexane/toluene, each successive eluting mixture containing 10% more toluene. The fraction eluted with 80% toluene contained 5[2'-(4-methylphenyl)-2-(1,3-dithiolanyl)]-1-methylpyrrole-2-acetonitrile. The solvent was evaporated in vacuo and the residue is crystallized from methanol to give 35 mg, m.p. 117°–119° C. Recrystallization from ethyl acetate-cyclohexane afforded white crystalline 5-[(2-4-methylphenyl)-2-(1,3-dithiolanyl)]-1-methylpyrrole-2-acetonitrile, m.p. 128°–130° C.

EXAMPLE IX 2-(4-Methylphenyl)-1,3-dithiolanium chloride

The U.V. spectrum of a solution of 1 mg 2,2'-[1,2-ethanediylbis (thio)]-2,2'-di(4-methylphenyl)bis(1,3-dithiolane) in 100 ml of 0.8% hydrogen chloride in methyl chloride is measured: max 243,275,376 nm, the latter indicating the presence of 2-(4-methylphenyl)-1,3-dithiolanium cation.

EXAMPLE X

A. 2-(4-Methylphenyl)-1,3-dithiolanium cation

A mixture of 1.63 g (0.01 mole) of N,N-dimethyl-4-methylbenzamide and 0.915 ml (0.01 mole of phosphorous oxychloride is heated at 60° for 2 hr under nitrogen. A 3 ml sample of methylene chloride is added, then a 1.05 ml (0.01 mole) sample of ethanedithiol. The mixture is stirred 1 hr. A sample of the reaction is diluted 4,100 fold with methylene chloride and its ultraviolet spectrum measured: max 255,270,376nm, the latter indicating the presence of 2-(4-methylphenyl)-1,3-dithiolanium cation.

B. 2-(4-Methylphenyl)-1,3-dithiolanium chloride

A solution of 1.96 g (0.01 mole) of 2-(4-methylphenyl)-1,3-dithiolane in 20 ml of methylene chloride is cooled to 0° C. and 0.76 ml (0.0094 mole) of sulfuryl chloride is added in one portion. The mixture is stirred 1 hr at 5° C. It is diluted with methylene chloride and the ultraviolet spectrum measured: U.V. max 230,255,375 nm, the latter indicating the presence of 2-(4-methylphenyl)-1,3-dithiolanium cation.

EXAMPLE XI

5-[2-(4-Methylphenyl)-2-(1,3-dithiolanyl)] 1-methylpyrrole-2-acetonitrile

A solution of 3.8 ml (0.047 mole) of sulfuryl chloride in 25 ml of methylene chloride is added dropwise over 15 min to a solution of 9.8 g (0.05 mole) of 2(4-methylphenyl)-1,3-dithiolane in 75 ml of methylene chloride. The mixture is stirred 3 hr at room temperature. It is cooled to 5° and a solution of 6.0 g (0.05 mole) of N-methylpyrrole-2-acetonitrile in 25 ml of $CH_2Cl_2$ is added rapidly. The mixture is stirred 2 hr at 5°. It is shaken with iced dilute sodium hydroxide. The organic layer is dried ($MgSO_4$) and the solvent evaporated in vacuo. The residue is crystallized from ethyl acetate-hexane (about 1:1) to give 2.4 g of a solid. It is recrystallized from ethyl acetate-hexane to give 1.6 g of crystalline 5-[2-(4-methylphenyl)-2-(1,3-dithiolanyl)]-1-methylpyrrole-2-acetonitrile, m.p. 128°–129° C.

EXAMPLE XII

5-[2-(4-methylphenyl)-2-(1,3-dithiolanyl)]-1-methylpyrrole-2-acetic acid methyl ester N,N-dimethyl-4-methylbenzamide 19.35 g. (0.119 mole) is heated under nitrogen with stirring in a three-necked round bottom flask to 55° and phosphorus oxychloride ($POCl_3$) 10.85 ml, (0.119 mole) added dropwise keeping the temperature at 50°–60° C., then stirred 2.25 hrs at 58°–60° C. Then 1,2-dichloroethane (30 ml) is added, the temperature of the reaction mixture lowered to 45° C., and a solution of ethanedithiol 9.9 ml, (0.119 mole) in 1,2-dichloroethane (30 ml) added dropwise keeping the temperature at 40°–50° C. The solution is then stirred at 45° C. for 2 hrs. This solution is then added dropwise to a solution of 1-methylpyrrole-2-acetic acid methyl ester 16.6 g (0.108 mole) in 200 ml of 1,2-dichloroethane under nitrogen (dry) at −5° to −10° C., then allowed to stir at −9° C. for 30 min after the addition is completed. The reaction mixture is then poured into a mixture of ice and 10% aqueous sodium hydroxide solution (500 ml of ice + 500 ml 10% NaOH) and shaken well until the color of the solution changes from deep red to light yellow. The organic layer is separated, washed with brine, dried over $MgSO_4$ (anhydrous powder), and evacuated in vacuo to a yellow oil which gradually crystallizes on cooling. Recrystallizing from cyclohexane once, and three times from methanol gives a white crystalline solid yield, 6.3 g (17.4%) and m.p. 113.5°–116.5° C.

EXAMPLE XIII

4-Chloro-5-[2-(4-chlorophenyl)-2-(1,3-dithiolanyl)] pyrrole-2-acetonitrile

A 14.6 ml (0.16 mole) sample of phosphorous oxychloride is added dropwise to 29.4 g (0.16 mole) of 4-chloro-N,N-dimethylbenzamide at 70° C. The mixture is heated 2 hr at 60°–70° C. A 50 ml sample of 1,2-dichloroethane is added. A 13.4 ml (0.16 mole) sample of ethanedithiol is added at a rate so the temperature stays below 50° C. It is stirred 1 hr at room temperature. The mixture is cooled to 5° C. and a solution of 22.5 g (0.16 mole) of 4-chloropyrrole-2-acetonitrile in 80 ml of 1,2-dichloroethane is added rapidly. The mixture is stirred for 1 hr at 5° C. and 1 hr at 25° C. It is poured into iced dilute sodium hydroxide. It is extracted with ether. The solution is charcoaled and the solvent is evaporated in vacuo. The residue is taken up in ether and charcoaled again. The solvent is evaporated in vacuo. The residue is crystallized from 2-propanol. A crop of crystals is obtained by decanting from tarry residue, 5.5 g, m.p. 128°–130° C. A second crop is obtained by triturating the residue with ether (10.6 g, m.p. 128°–130° C.). The ether filtrate is evaporated and a third crop (9.1 g, m.p. 117°–121° C.) taken from toluene. The third crop is recrystallized from methanol. It is combined with the first and second crops and recrystallized from 2-propanol to give 17.0 g of 4-chloro-5-[2-(4-chlorophenyl)2(-1,3-dithiolanyl)]pyrrole-2-acetonitrile, m.p. 133°–135° C.

EXAMPLE XIV

4-Chloro-5-(4-chlorobenzoyl)-pyrrole-2-acetonitrile

A solution of 16.0 g (0.0455 mole) of 4-chloro-5[2(4-chlorophenyl)-1,3-dithiolanyl)]pyrrole-2-acetonitrile and 28 ml (0.45 mole) of methyl iodide in 480 ml of methanol and 20 ml of water is heated under reflux for 18 hr. It is poured into sodium bicarbonate solution. The precipitated solid is collected and washed with cold methanol to give 9.0 g of solid m.p. 184°–192° C. Recrystallization from ethyl (acetate gives 4.5 g of 4-chloro-5-(4-chlorobenzoyl)-pyrrole-2-acetonitrile, m.p. 199°–200° C.

EXAMPLE XV 2-(4-Chlorophenyl)1,3-dithiolanium chloride

The U.V. spectrum of a solution of 1 mg of 2,2'-[1,2-ethanediylbis (thio)]-2,2'-di(4-chlorophenyl)bis(1,3-dithiolane in 100 ml of 1% hydrogen chloride in methylene chloride is measured. λmax 249,271,372 nm; the latter indicating the presence of 2-(4-chlorophenyl)1,3-dithiolanium cation.

I claim:

1. A method of preparing a compound having the formula:

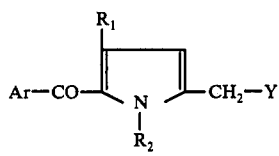

which comprises reacting a 2-Ar-1,3-dithiolanium salt having the formula:

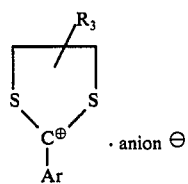

with a compound having the formula:

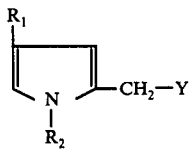

in an inert organic solvent at a temperature from about −70° C. to about 25° C. to yield a compound having the formula:

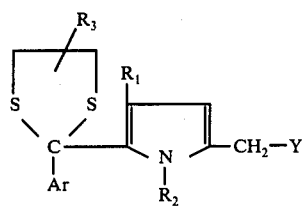

and subsequently hydrolyzing (IV) to yield the compound of formula (I) by treatment of (IV) with methyl iodide or dimethyl sulfate in an aqueous lower alkanolic solvent or by treatment of (IV) with alkali in aqueous or aqueous alkanolic solution at 70°–180° C., wherein the foregoing formulas:

$R_1$ is a member selected from the group consisting of hydrogen, chloro and bromo;

$R_2$ is a member selected from the group consisting of hydrogen and loweralkyl;

$R_3$ is a member selected from the group consisting of hydrogen and loweralkyl;

Y is a member selected from the group consisting of CN, COOH and COO-loweralkyl; and Ar is a member selected from the group consisting of phenyl, thienyl, trifluoromethylphenyl, methylthiophenyl and phenyl substituted with from one to three members each selected from the group consisting of halo, loweralkyl, and loweralkoxy.

2. The method of claim 1 wherein said (IV) is hydrolyzed by treatment with methyl iodide in aqueous methanol.

3. The method of claim 1 wherein said (IV) is hydrolyzed by treatment with sodium hydroxide in aqueous alkanolic solution at a temperature of about 70°–180° C.

4. A method of preparing a compound having the formula:

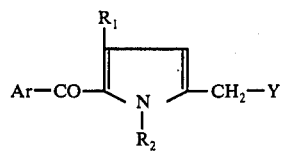

which comprises reacting a solution containing a 2-Ar-1,3-dithiolanium salt having the formula:

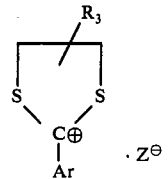

obtained by treating a Vilsmeier reagent having the formula:

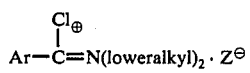

with ethanedithiol, with a compound having the formula:

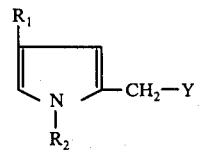

in an inert organic solvent at a temperature from about −70° C. to about 25° C. to yield a compound having the formula:

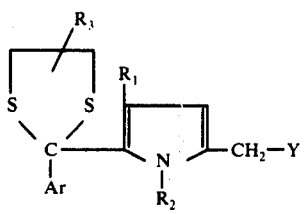
(IV)

and subsequently hydrolyzing (IV) to yield the compound of formula (I) by treatment of (IV) with methyl iodide or dimethyl sulfate in an aqueous lower alkanolic solvent or by treatment of (IV) with alkali in aqueous or aqueous alkanolic solution at 70°–180° C., wherein the foregoing formulas:

$R_1$ is a member selected from the group consisting of hydrogen, chloro and bromo;

$R_2$ is a member selected from the group consisting of hydrogen and loweralkyl;

$R_3$ is a member selected from the group consisting of hydrogen and loweralkyl;

Z is a member selected from the group consisting of $Cl^{\ominus}$ and $PO_2Cl_2^{\ominus}$;

Y is a member selected from the group consisting of CN, COOH and COO-loweralkyl; and Ar is a member selected from the group consisting of phenyl, thienyl, trifluoromethylphenyl, methylthiophenyl and phenyl substituted with from one to three members each selected from the group consisting of halo, loweralkyl, and loweralkoxy.

5. A method of preparing a compound having the formula:

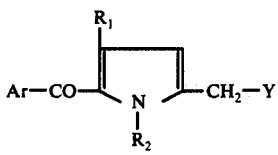
(I)

which comprises reacting a solution containing a 2-Ar-1,3-dithiolanium salt having the formula:

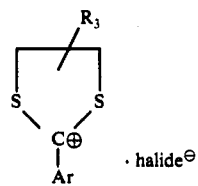
(II-b)

obtained by halogenating a 2-aryl-1,3-dithiolane having the formula:

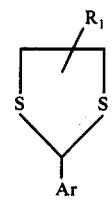

in a reaction-inert organic solvent, with a compound having the formula:

$$\text{(III)}$$

in an inert organic solvent at a temperature from about −70° C. to about 25° C. to yield a compound having the formula:

(IV)

and subsequently hydrolyzing (IV) to yield the compound of formula (I) by treatment of (IV) with methyl iodide or dimethyl sulfate in an aqueous lower alkanolic solvent or by treatment of (IV) with alkali in aqueous or aqueous alkanolic solution at 70°–180° C., wherein the foregoing formulas:

$R_1$ is a member selected from the group consisting of hydrogen, chloro and bromo;

$R_2$ is a member selected from the group consisting of hydrogen and loweralkyl;

$R_3$ is a member selected from the group consisting of hydrogen and loweralkyl;

Y is a member selected from the group consisting of CN, COOH and COO-loweralkyl; and Ar is a member selected from the group consisting of phenyl, thienyl, trifluoromethylphenyl, methylthiophenyl and phenyl substituted with from one to three members each selected from the group consisting of halo, loweralkyl, and loweralkoxy.

* * * * *